United States Patent
Sosic et al.

(10) Patent No.: US 10,317,376 B2
(45) Date of Patent: Jun. 11, 2019

(54) METHODS OF DETECTING GLYCOSAMINOGLYCANS

(71) Applicant: Bioverativ Therapeutics Inc., Waltham, MA (US)

(72) Inventors: Zoran Sosic, Cambridge, MA (US); Andrew Blum, Wilmington, MA (US); Bing Guan, Needham, MA (US); Boris Boumajny, Northborough, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 103 days.

(21) Appl. No.: 14/391,775

(22) PCT Filed: Apr. 11, 2013

(86) PCT No.: PCT/US2013/036205
§ 371 (c)(1),
(2) Date: Oct. 10, 2014

(87) PCT Pub. No.: WO2013/155324
PCT Pub. Date: Oct. 17, 2013

(65) Prior Publication Data
US 2015/0075261 A1 Mar. 19, 2015

Related U.S. Application Data

(60) Provisional application No. 61/622,720, filed on Apr. 11, 2012.

(51) Int. Cl.
*G01N 30/60* (2006.01)
*C08B 37/00* (2006.01)
(Continued)

(52) U.S. Cl.
CPC ......... *G01N 30/60* (2013.01); *C08B 37/0003* (2013.01); *C08B 37/0021* (2013.01);
(Continued)

(58) Field of Classification Search
None
See application file for complete search history.

(56) References Cited

U.S. PATENT DOCUMENTS

| | | | |
|---|---|---|---|
| 5,914,390 A | 6/1999 | Nathan et al. | |
| 6,870,034 B2 * | 3/2005 | Breece | C07K 1/22 |
| | | | 436/824 |

(Continued)

FOREIGN PATENT DOCUMENTS

| | | |
|---|---|---|
| JP | 2003-279553 A | 10/2003 |
| JP | 2004-203747 A | 7/2004 |

(Continued)

OTHER PUBLICATIONS

Araki et al., "Application of 2-aminopyridine fluorescence labeling in the analysis of in vivo and in vitro metabolism of dextran sulfate sodium by size-exclusion high-performance liquid chromatography", Journal of Chromatography B: Biomedical Sciences and Applications, vol. 753, Issue 2, Apr. 5, 2001, pp. 209-215.*

(Continued)

*Primary Examiner* — Leslie J Evanisko
*Assistant Examiner* — Quang X Nguyen
(74) *Attorney, Agent, or Firm* — Lathrop Gage LLP; James H. Velema, Esq.

(57) ABSTRACT

In one aspect, the disclosure provides methods of distinguishing a glycosaminoglycan from one or more other components in a sample by subjecting the sample to size-exclusion chromatography using a mobile phase having a pH of 6.8 or lower. A mobile phase having a pH of 6.8 or lower is found to improve the separation of glycosaminoglycans from proteins during size exclusion chromatography. In some embodiments, improved separation is due to the low pH of the mobile phase causing elution of less dispersed fractions of the protein and/or glycosaminoglycan.

(Continued)

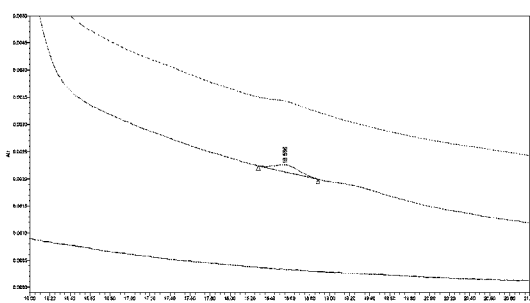

Representative Overlaid Zoomed-in Chromatograms for FIXFc Drug Substance Formulation Buffer Blank (bottom line), FIXFc Drug Substance LP5-10-FIX-001 (top line), and 2 μg/mL Dextran Sulfate Spiked into FIXFc Drug Substance LP5-10-FIX-001 (middle line), respectively In some embodiments, the overlap between protein and/or glycosaminoglycan fractions is reduced.

19 Claims, 1 Drawing Sheet

(51) Int. Cl.
*C08B 37/02* (2006.01)
*G01N 30/02* (2006.01)
*G01N 33/68* (2006.01)

(52) U.S. Cl.
CPC ...... *C08B 37/0063* (2013.01); *G01N 33/6842* (2013.01); *G01N 2030/027* (2013.01); *G01N 2400/40* (2013.01)

(56) References Cited

U.S. PATENT DOCUMENTS

| | | | |
|---|---|---|---|
| 7,276,580 B2 | 10/2007 | Sah et al. | |
| 7,790,466 B1 * | 9/2010 | Shriver | G01N 30/96 210/656 |
| 2005/0238536 A1 | 10/2005 | Striepeke et al. | |

FOREIGN PATENT DOCUMENTS

| | | |
|---|---|---|
| JP | 2004-203747 A | 7/2009 |
| JP | 2009-270966 A | 11/2009 |
| WO | WO 2004/069176 A2 | 8/2004 |
| WO | WO 2004/094592 A2 | 11/2004 |
| WO | WO 2006/023791 A2 | 3/2006 |
| WO | WO 2010/071817 A2 | 6/2010 |
| WO | WO 2011/062561 A1 | 5/2011 |
| WO | WO 2011/069164 A2 | 6/2011 |
| WO | WO 2012/006624 A2 | 1/2012 |
| WO | WO 2012/170969 A2 | 12/2012 |
| WO | WO 2013/009627 A2 | 1/2013 |
| WO | WO 2013/012733 A1 | 1/2013 |
| WO | WO 2013/016454 A1 | 1/2013 |

OTHER PUBLICATIONS

COSMOSIL Diol-120 Datasheet (Apr. 7, 2011).*
Thermo Hypersil Brochure, published 2010.*
Araki et al., Application of 2-aminopyridine fluorescence labeling in the analysis of in vivo and in vitro metabolism of dextran sulfate sodium by size-exclusion high-performance liquid chromatography. J Chromatogr B Biomed Sci Appl. Apr. 5, 2001;753(2):209-15.
Chaidedgumjorn et al., Conductivity detection for molecular mass estimation of per-O sulfonated glycosaminoglycans separated by high-performance size-exclusion chromatography. J. Chromatogr A. Jun. 14, 2002;959(1-2):95-102.
Doneanu et al., Impurity evaluation of heparin sodium by anion exchange chromatography. Waters Corporation. Nov. 2008 4 pages.
Maderich et al., Size-exclusion chromatographic determination of dextran sulfate in rat serum. J Chromatogr. Oct. 22, 1993;620(1):137-42.
No Author Listed, Analysis of hydrophilic polymers-dextran sulfate. Shodex. Accessed online Dec. 7, 2010 www.shodex.com/english/dc061333.html. 1 page.
No Author Listed, Dextran sulfate 5000 ELISA kit for buffer/urine samples. Lifespan Technologies. Oct. 20, 2008. 2 pages.
No Author Listed, Dextran sulfate technical information. Imtakt Corp.
Extended European Search Report dated Nov. 10, 2015 for Application No. EP 13776381.9.
Araki et al., Chemical depolymerization of dextran sulfate sodium—the application of size-exclusion or ion-pair liquid chromatography. Biomed Chromatogr. Apr. 2007;21(4):335-7.
Martins et al., Molecular size distribution analysis of human gingival glycosaminoglycans in cyclosporin- and nifedipine-induced overgrowths. J Periodontal Res. Apr. 2003;38(2):182-9.

* cited by examiner

Figure 1) Linearity Plot for FIXFc Drug Substance (LP5-10-FIX-001) Samples Spiked with Dextran Sulfate Standard to 1, 2, 5, 10, 20, and 50 µg/mL Final Concentrations

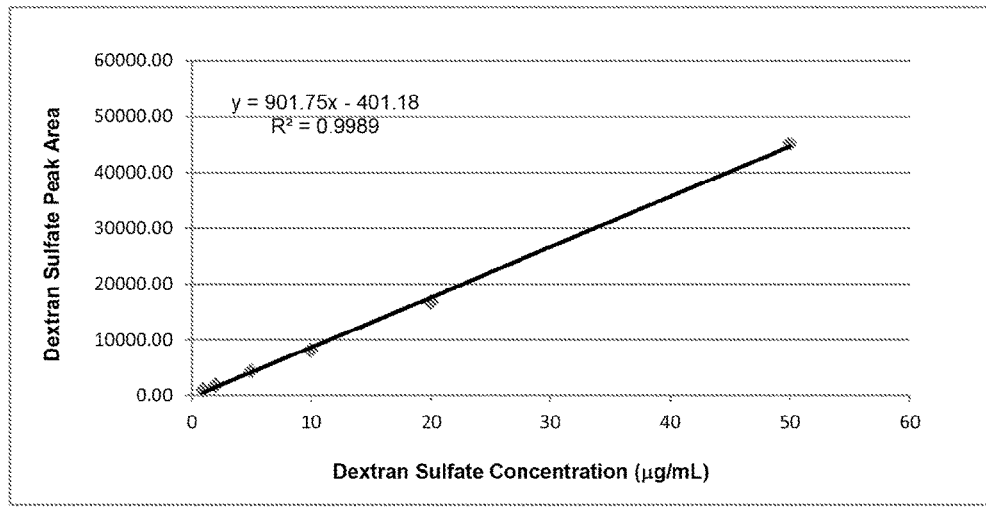

Figure 2) Representative Overlaid Zoomed-in Chromatograms for FIXFc Drug Substance Formulation Buffer Blank (bottom line), FIXFc Drug Substance LP5-10-FIX-001 (top line), and 2 µg/mL Dextran Sulfate Spiked into FIXFc Drug Substance LP5-10-FIX-001 (middle line), respectively

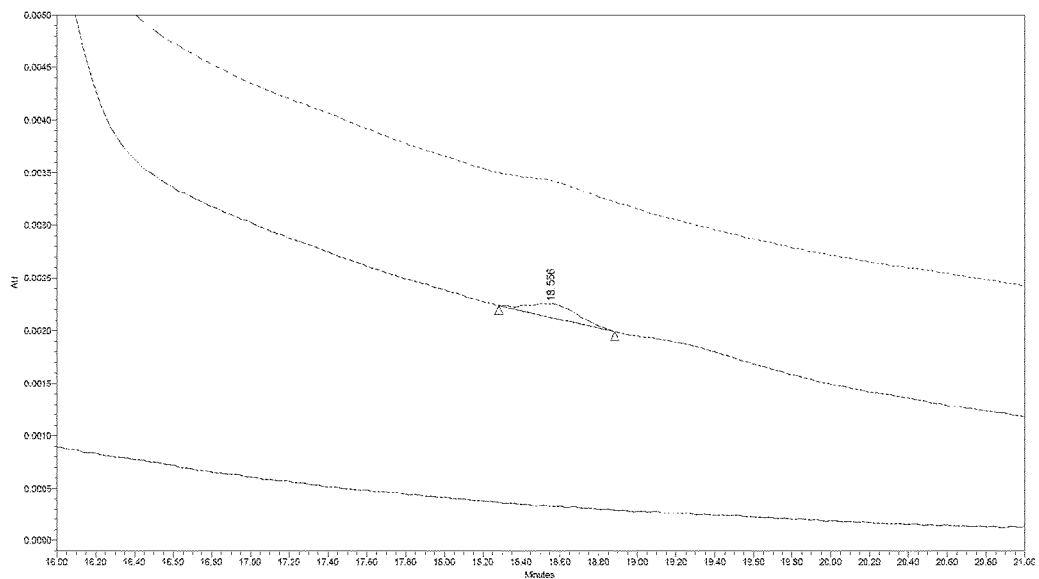

METHODS OF DETECTING GLYCOSAMINOGLYCANS

RELATED APPLICATIONS

This application is a national stage filing under 35 U.S.C. § 371 of international application PCT/US2013/036205, filed Apr. 11, 2013, which was published under PCT Article 21(2) in English and claims the benefit under 35 U.S.C. § 119(e) of U.S. provisional application Ser. No. 61/622,720, filed Apr. 11, 2012, each of which is herein incorporated by reference in its entirety.

FIELD OF THE INVENTION

The invention relates to the analysis and separation of biological samples.

BACKGROUND

Recombinant and synthetic protein samples often include unwanted non-protein components that result from the protein production process. New methods for distinguishing these non-protein components from recombinant or synthetic proteins are needed to improve the production of proteins of interest.

SUMMARY OF THE INVENTION

In some embodiments, aspects of the invention provide simple chromatographic techniques that can be used to evaluate the presence or amount of glycosaminoglycan in a protein sample. Glycosaminoglycans were found to be affected by the pH of the mobile phase during size exclusion chromatography. Surprisingly, a mobile phase having a pH below neutral significantly delays the migration of glycosaminoglycan fractions relative to other components in a protein sample. Also, the migration of glycosaminoglycan fractions is significantly less dispersed when using a mobile phase at lower than neutral pH. This allows for increased sensitivity of glycosaminoglycan detection without complex sample processing.

Accordingly, in some embodiments, aspects of the invention relate to methods and compositions for distinguishing glycosaminoglycans from proteins and other components in a sample, for example in a sample obtained from a protein production process. Glycosaminoglycans can be used during protein production to increase the yield of recombinant protein (See e.g., U.S. Pat. No. 5,914,390). For instance, glycosaminoglycans can be added to cell culture media during the production of blood cascade proteins or other recombinant proteins.

Methods described herein can be used for both analytical and preparative applications. In some embodiments, a sample can be evaluated to determine the purity of one or more proteins relative to one or more glycosaminoglycans in the sample. In some embodiments, one or more proteins can be separated and isolated from one or more glycosaminoglycans in a sample. These applications can be useful, for example, in the context of a protein production and/or isolation procedure.

In some embodiments, methods and compositions are related to the unexpected behavior of proteins and glycosaminoglycans during size exclusion chromatography performed at below neutral pH (e.g., pH 6.8 or lower). A mobile phase having a pH of 6.8 or lower is found to improve the separation of glycosaminoglycans from proteins during size exclusion chromatography. In some embodiments, improved separation is due to the low pH of the mobile phase causing elution of less dispersed fractions of the protein and/or glycosaminoglycan. In some embodiments, the overlap between protein and/or glycosaminoglycan fractions is reduced.

In some embodiments, a method of distinguishing a glycosaminoglycan from one or more other components in a sample comprises subjecting a sample to size-exclusion chromatography using a mobile phase having a pH of 6.8 or lower. In some embodiments, a detection device is used to determine an amount of glycosaminoglycan in the mobile phase that has been subjected to the size-exclusion chromatography, for example to determine the amount of glycosaminoglycan in the sample. Accordingly, in some embodiments a method of determining whether a sample contains glycosaminoglycan includes applying a sample to a size-exclusion column, applying a mobile phase having a pH of 6.8 or lower to run the sample through the size-exclusion column, and using a detection device to determine whether glycosaminoglycan is present in the mobile phase that has run through the column, thereby determining whether the sample contains glycosaminoglycan.

In some embodiments, methods described herein can be used to determine whether an amount of glycosaminoglycan in a sample is above a threshold level. In some embodiments, the threshold level is 2 microgram/ml.

In some embodiments, methods described herein can be used to separate glycosaminoglycan from a sample.

In some embodiments, a sample being processed according to methods described herein contains protein. In some embodiments, a sample is unpurified or partially purified.

In some embodiments, a sample contains one or more blood cascade proteins, for example, but not limited to, Factor VIII-Fc or Factor IX-Fc.

In some embodiments, a negatively charged glycosaminoglycan is resolved from a protein. In some embodiments, the glycosaminoglycan is dextran sulfate. In some embodiments, the dextran sulfate has a size of 6-8 kDa. In some embodiments, the glycosaminoglycan is heparin sulfate.

In some embodiments, a detection device used to detect a glycosaminoglycan is a UV detector.

In some embodiments, size-exclusion chromatography is performed using a chromatography packing material. In some embodiments, the packing material allows for secondary interactions with the mobile phase that is used. In some embodiments, the size-exclusion chromatography packing material is silica-based. In some embodiments, the size-exclusion chromatography packing material has a pore size of 100-200 Angstrom. In some embodiments, the packing material has a particle size of 5 microns or less.

In some embodiments, the pH of the mobile phase is 6.0 or lower, 5.0 or lower, 4.0 or lower, 3.0 or lower, or 2.5 or lower. In some embodiments, the mobile phase comprises salt. In some embodiments, the salt is 200 mM NaCl.

These and other aspects of the invention are described and illustrated in the following detailed description, examples, and claims.

BRIEF DESCRIPTION OF THE DRAWINGS

The figures are illustrative only and are not required for enablement of the invention disclosed herein.

FIG. 1 shows the linearity plot for a Factor IX-Fc sample (LP5-10-FIX-001) spiked with dextran sulfate standards.

FIG. 2 shows a calibration curve for dextran sulfate standards, and several zoomed-in chromatograms including Factor IX-Fc sample alone, Factor IX-Fc formulation buffer alone, and Factor IX-Fc sample spiked with 2 microgram/mL of dextran sulfate (6-8 kDa).

DETAILED DESCRIPTION OF THE INVENTION

In some embodiments, aspects of the invention relate to methods and compositions for enhancing the sensitivity of glycosaminoglycan detection in samples that contain proteins and/or other components. In some embodiments, methods are provided for distinguishing glycosaminoglycans from proteins in a sample by increasing the separation between the glycosaminoglycans and proteins when using size exclusion chromatography. In some embodiments, methods are provided for separating glycosaminoglycans from proteins in a sample by increasing the separation between the glycosaminoglycans and proteins when using size exclusion chromatography. In some embodiments, the elution profile of glycosaminoglycans from size exclusion chromatography material is less dispersed when using methods and compositions described herein instead of standard chromatography conditions.

In some embodiments, aspects of the invention are useful to detect small amounts of contaminating glycosaminoglycans in a protein sample using simple detection devices. This provides a significant improvement over current analytical techniques that require more complex procedures, such as protein removal, or more sample material, and often fail to detect small amounts of glycosaminoglycans. The ability to effectively distinguish glycosaminoglycans from proteins can be used to evaluate the presence and amount of glycosaminoglycans in a sample more reproducibly. This is useful, for example, in the context of protein production and purification when it can be important to remove contaminating glycosaminoglycans (e.g., dextran sulfate, heparin sulfate, or other glycosaminoglycans). In some embodiments, the ability to detect small amounts of glycosaminoglycans is useful as a quality control tool to identify protein samples that are likely to be less effective due to the presence of small amounts of glycosaminoglycans. However, it should be appreciated that aspects of the invention are not limited to analytical applications, but also can be used for preparative purposes to help isolate or purify proteins.

Aspects of the invention are based, at least in part, on the unexpected effect of a mobile phase at below neutral pH on the elution of glycosaminoglycans from size exclusion chromatography material. In some embodiments, a mobile phase at below neutral pH improves the separation of glycosaminoglycans from proteins and/or other components in a sample, thereby reducing the overlap of their elution profiles. In some embodiments, a mobile phase at below neutral pH tightens (i.e., is less dispersed) the elution profile of glycosaminoglycans, thereby increasing the ability to detect small amounts of glycosaminoglycans, and allowing simple detection devices (e.g., a UV detector) to be used. Accordingly, methods provided herein are useful for determining the presence of glycosaminoglycan(s) in a sample at lower levels than was previously possible, and using simpler devices than was previously possible. While not being limited to a specific mechanism it is thought that the below neutral pH minimizes the ionic-interactions of protein and/or glycosaminoglycans with the stationary phase of the column.

Current methods for detecting a glycosaminoglycan such as dextran sulfate in a sample are limited to low protein samples (such as urine or buffers). More concentrated protein samples, for example samples obtained from a protein production procedure, currently require processing to remove protein before assaying for the presence or amount of a glycosaminoglycan. Current methods are cumbersome and require labeling of dextran with a fluorescent dye or the use of expensive high resolution methods such as 2D-Liquid Chromatography (See e.g., Maderich et al., 1993, J. of Chromatography 620: 137-142; Araki et al., 2001, J. of Chromatography B 753: 209-215). However, even the use of fluorescent labeling and/or 2D-LC generally still requires purification steps to remove some or all of the protein.

In contrast, methods described herein allow glycosaminoglycans in concentrated protein samples to be distinguished and quantified with high sensitivity using a single procedure and simple separation and detection devices. For example, methods described herein allow protein samples to be evaluated for the presence of low threshold levels (e.g., 10 microg/ml, 5 microg/ml, 2 microg/ml, 1 microg/ml, or lower) of one or more glycosaminoglycans (e.g., dextran sulfate, heparin sulfate, etc.). Accordingly, low levels of glycosaminoglycans can be effectively detected in the presence of proteins, salt, and other components such as surfactants (e.g., Tween-20, Tween-80) and polypropylene glycol. However, it should be appreciated that higher levels of glycosaminoglycans also may be detected and/or removed, as aspects of the invention are not limited to the removal or detection of low levels of glycosaminoglycans.

It should be understood that size exclusion chromatography was not expected to allow glycosaminoglycan to be effectively separated from proteins, particularly in the context of concentrated protein samples. Using current methodologies, glycosaminoglycans and proteins overlap (partially or completely) when run through a size separation column. Glycosaminoglycans also tend to bind to proteins or other components in a sample, preventing them from being effectively separated. As a result, glycosaminoglycans are not readily detectable using current size exclusion techniques and complex techniques (e.g., specific labeling) would be required to distinguish them from proteins. In contrast, the methods described herein resolve glycosaminoglycans from proteins sufficiently to allow for independent detection of each of the components using simple techniques (e.g., spectrophotometry). In some embodiments, protein and glycosaminoglycan fractions can be detected and/or quantified using a standard UV spectrophotometer (e.g., using wavelengths of between 200-300 nm, such as 214 nm), without using any protein or glycosaminoglycan specific detection or binding reagent. Because the glycosaminoglycan and protein components are sufficiently resolved, a single technique that detects both components (e.g., a spectrophotometer or simple UV detector that detects signal from a particular wavelength or range of wavelengths) can be used to independently evaluate and quantify glycosaminoglycans and proteins and/or other components. However, it should be appreciated that techniques described herein can be used with glycosaminoglycan specific detection or binding reagents as aspects of the disclosure are not limited in this respect.

Samples

In some embodiments, methods and compositions described herein are useful for distinguishing glycosaminoglycans from other components in protein samples, for example concentrated protein samples, for example samples of therapeutic proteins.

In some embodiments, the sample is a biological sample. A biological sample, as used herein, is any sample that includes one or more biological components such as nucleic acids, polypeptides, microorganisms or eukaryotic cells. In some embodiments, the sample is a manufacturing sample. A manufacturing sample, as used herein, is any sample that is being used to produce a biological component, such as a nucleic acid or polypeptide (e.g., a therapeutic protein). In some embodiments, a manufacturing sample comprises microorganisms (e.g., E. coli) or eukaryotic cells (e.g., CHO cells), including lysates of microorganisms and eukaryotic cells. In some embodiments, the sample comprises a protein.

In some embodiments, the sample is unpurified. An unpurified sample as used herein refers to a sample that has not undergone any purification steps except for the removal of insoluble components. Unpurified samples include biological samples (e.g., plasma, blood, urine), from which insoluble particles have been removed, e.g., by centrifugation or filtration, but which have not undergone any purification step to remove soluble elements (e.g., nucleic acids, salts). Unpurified samples also can include manufacturing samples. Unpurified manufacturing samples include cell lysates and cell supernatants from which insoluble debris has been removed but that have not undergone purification step to remove soluble elements (e.g., salts). In some embodiments, an unpurified sample is a supernatant from a fermentation process.

In some embodiments, the sample is partially purified. A partially purified sample, as used herein, refers to a sample from which one or more soluble components have been removed. Components that have been removed from a partially purified sample include, for instance, sugars, salts, dyes and nutrients (e.g., amino acids). The removal of the one or more soluble components can be partial or complete. In some embodiments, the sample is partially purified through one or more dialysis steps. In addition, in a partially purified sample insoluble components may also have been removed.

In some embodiments, the sample comprises protein (or a polypeptide). Both biological samples and manufacturing samples generally include protein. The methods provided herein can be practiced both on samples that are high in protein, such as manufacturing samples, e.g., cell lysates, and blood, and samples that are low in protein, such as buffers and urine.

In some embodiments, the sample comprises one or more therapeutic proteins for production. In some embodiments the protein production sample is a sample of recombinantly produced protein. In some embodiments, the sample contains proteins that are harvested from plasma. In some embodiments, the sample comprises proteins that can bind glycosaminoglycans, In some embodiments, the sample includes one or more blood cascade proteins (e.g., coagulation factors). Blood cascade proteins are known in the art and include, but are not limited to, Factor VII, tissue factor, Factor IX, Factor X, Factor XI, Factor XII, Tissue factor pathway inhibitor, Factor V, prothrombin, thrombin, vonWillebrand Factor, kininogen, prekallikrien, kallikrein, fribronogen, fibrin, protein C, thrombomodulin, Factor IV, Factor VI, Factor VIII, fibronectin, heparin cofactor, protein S, protein Z, protein Z-related protease inhibitor, plasminogen, alpha-2-antiplasmin, tissue plasminogen activator, urokinase, plasminogen activator inhibitor-1, plasminogen activator inhibitor-2, and antithrombin. In some embodiments, the blood cascade protein is Factor IX or Factor VIII. Assays for determining Factor VIII and Factor IX activity are described for instance in WO2013/016454. In some embodiments, the blood cascade protein is a human protein. In some embodiments, the blood cascade protein is used in therapy, for instance, in a subject that is deficient in one or more blood cascade proteins (e.g., a subject having hemophilia).

It should be appreciated that the methods are also applicable to samples comprising modified versions of blood cascade proteins and polypeptides comprising a blood cascade proteins. In some embodiments, the blood cascade proteins are covalently bound to other proteins. In some embodiments, the blood cascade proteins are covalently bound to antibodies or antibody fragments, such as Fc. In some embodiments, the blood cascade protein is Factor IX-Fc (FIXFc) or Factor VIII-Fc (FVIIIFc). Chimeric blood clotting factors-Fc conjugates are described for instance in WO2013/012733, WO2013/009627, WO2012/170969, WO2012/006624, and WO2011/069164, which are incorporated specifically herein in their entirety.

Blood cascade proteins are often administered to subjects who have difficulties in regulating homeostasis, such as subjects suffering from hemophilia. If a therapeutic that includes coagulation inducing/stimulating proteins is administered to a subject it is very important that such a therapeutic is free of anticoagulants. In some embodiments, the disclosure provides methods of removing anticoagulants, such as glycosaminoglycans, from blood cascade protein samples. In some embodiments, the disclosure provides methods for detecting if a sample that includes blood cascade proteins contains an amount of anticoagulant that is below a certain level. In some embodiments, the disclosure provides methods for detecting if a sample that includes blood cascade proteins contains an amount of anticoagulant small enough to render the sample ready for downstream processing (e.g., preparing as a pharmaceutical composition to be administered).

In some embodiments, the sample includes protein hormones, regulatory proteins and/or neurotrophic factors. Neurotrophic factors are known in the art and include nerve growth factor (NGF), brain-derived neurotrophic factor (BDNF), neurotrophin-3 (NT-3), neurotrophin-4 (NT-4), members of the glial cell line-derived neurotrophic factor ligands (GDNF), nerterin, artemin, persephin, and ciliary neurotrophic factor (CNTF). In some embodiments, the sample includes neublastin (See e.g., U.S. Pat. No. 7,276,580, which is incorporated specifically herein in its entirety). In some embodiments, the neurotrophic factor is a human protein. In some embodiments, the neurotrophic factor is used in therapy, for instance, in subjects that are suffering from peripheral neuropathy and associated pain syndroms.

It should be appreciated that the methods are also applicable to samples comprising modified versions of neurotrophic factors and polypeptides comprising neurotrophic factors. In some embodiments, the neurotrophic factors are covalently bound to other proteins. In some embodiments, the neurotrophic factors are covalently bound to antibodies or antibody fragments, such as Fc. In some embodiments, the sample includes variants of neublastin (See e.g., WO2006/023791, which is incorporated specifically herein in its entirety). In some embodiments, the sample includes conjugates of neublastin (See e.g., W2004/094592 and WO2004/069176, which are incorporated specifically herein in their entirety).

During the production process of blood cascade proteins or other proteins, anticoagulants can be added to optimize production. The anticoagulant is to be removed and/or be below a certain level before the protein sample (e.g., blood cascade protein sample) can be further processed or administered. Methods disclosed herein allow for the determination of the amount of anticoagulant, such as glycosaminoglycan in a sample prior to further processing or administration. In some embodiments, the protein is not removed from the sample in which the amount of glycosaminoglycan is to be determined.

It should be appreciated that methods described herein are useful for samples that contain glycosaminoglycans. Glycosaminoglycans are unbranched polysaccharides consisting of a repeating disaccharide unit. The repeating unit consists of a hexose or hexuronic acid linked to a hexosamine. Many of the glycosaminoglycans are negatively charged and include sulfate groups. Glycosaminoglycans include dextran sulfate, chondroitin sulfate, dermatan sulfate, keratin sulfate, heparin, heparin sulfate, and hyaluronan. Glycosaminoglycans are naturally produced in the human body. Glycosaminoglycans are found in nature with a variety of polymer lengths. In addition, glycosaminoglycans can be modified and/or purified to generate glycosaminoglycans with a desired polymer length (e.g., desired kDa).

In some aspect, the glycosaminoglycans of the methods disclosed herein have specific characteristics. In some embodiments, the glycosaminoglycan is negatively charged. In some embodiments, the glycosaminoglycan is dextran sulfate. In some embodiments, the glycosaminoglycan is about 6-8 kDa in size. In some embodiments, the glycosaminoglycan is dextran sulfate of about 6-8 kDa in size. In some embodiments, the glycosaminoglycan is heparin sulfate.

In some embodiments, concentrated protein samples (e.g., samples high in protein content) include, but are not limited to, protein samples obtained from recombinant protein expression preparations.

Chromatography

In some embodiments, glycosaminoglycans are separated from other components in a sample by using size exclusion chromatography with a mobile phase that has a pH of 6.8 or less. Size exclusion chromatography is a separation technology based on size and molecular weight of the components in the sample. A size exclusion column generally comprises silica particles of a specific pore size resulting in a "maze" through which the sample components travel. Smaller particles get stuck and delayed in the column pores while larger particles that do not fit in the pores elute from the column first.

In some embodiments, the methods disclosed herein include the element of subjecting a sample to size-exclusion chromatography. In some embodiments, subjecting a sample to size-exclusion chromatography comprises applying a sample onto a size-exclusion chromatography column. In some embodiments, applying a sample onto a size-exclusion chromatography column comprises contacting a size-exclusion chromatography column with a sample.

It should further be appreciated that the sample may be applied onto the column as one aliquot or in multiple batches. In some embodiments, the sample is a liquid solution. In some embodiments, the sample is a solid or emulsion that can be dissolved after application of the mobile phase. In some embodiments, the size-exclusion chromatography column is washed (e.g., with buffer) prior to applying a sample. The size-exclusion chromatography column may also be washed after applying a sample. Generally, a sample that has been applied onto a size-exclusion chromatography column will be run through the column by applying a mobile phase to the column.

It should be appreciated that size exclusion chromatography (SEC) can be performed in any suitable format, including columns of different sizes, including microfluidic channels, and other formats since aspect of the invention are not limited in this respect.

In some embodiments, the chromatography is performed using perfusion chromatography. In some embodiments, the chromatography is performed using anion-exchange chromatography.

It should be appreciated that multiple chromatography steps can be performed according to the methods described herein. Thus, for instance, a sample can be subjected to a first size exclusion chromatography step and subsequently to a second size exclusion chromatography step, or e.g., a sample can be subjected to a perfusion chromatography step followed by a size exclusion chromatography step. The choice of chromatography may depend, for instance, on the nature of the sample, with a complex sample more likely to undergo multiple purification steps.

It should be appreciated that size exclusion chromatography (SEC) can be performed under any suitable temperature and pressure conditions since aspects of the invention are not limited in this respect. For instance, one or more chromatography steps may be performed at 4° C., at room temperature or at higher temperatures (e.g., 40° C.). In general, the pressure used during chromatography will depend on the column, column material and operating conditions. Exemplary pressures are between 500-2000 psi, for instance 900-1000 psi.

It should be appreciated that size exclusion chromatography (SEC) disclosed herein are not limited to specific instrumentation and can be performed on any commercially available HPLC (High Performance Liquid Chromatography) instrument. HPLC instrumentation is available from a variety of vendors including Waters (Milford, Mass.), Agilent (Santa Clara, Calif.) and Shimadzu (Nakagyo, Japan).

It should be appreciated that different chromatographic materials may be used. In some embodiments, a silica-based chromatographic packing material may be used. In some embodiments, a packing material has a pore size of between 50 and 1000 Angstroms. In some embodiments, a packing material has a pore size of between 75 and 500 Angstroms. In some embodiments, a packing material has a pore size of between 100 and 200 Angstroms. In some embodiments, the packing material has a pore size of about 125 Angstroms. However, smaller or larger pore sizes may be used. In some embodiments, a packing material has a particle diameter of between 2-30 microns. In some embodiments, a packing material has a particle diameter of around 5, 8, 10, 13 or 17 microns. In some embodiments, a packing material has a particle diameter of 5 microns or less.

In some embodiments, a silica-based gel referred to as TSKgel G2000SWxl column (available from Tosoh, King of Prussia, Pa.) is used. However, it should be appreciated that other silica-based gels (e.g., Zenix SEC-150 from Sepax, Newark, Del.) could be used as aspects of the invention are not limited in this respect.

In some embodiments, without wishing to be limited by theory, the conditions used for chromatography promote secondary interactions between the glycosaminoglycan (e.g., dextran sulfate) and the chromatography material. In some embodiments, the chromatography material carries a hydroxyl group. In some embodiments, the chromatography material is a silica-based gel carrying a hydroxyl group. In some embodiments, these interactions help separate the glycosaminoglycan from the protein and other components in a sample by delaying the migration of the glycosaminoglycan through the chromatography material. In some embodiments, these interactions result in the concentration of the glycosaminoglycan fraction as it migrates through the column, thereby generating a narrower elution peak/profile.

Detector

In one aspect of the methods provided herein a detection device is used to determine the presence of components of interest in a sample. In some embodiments, the component of interest is a glycosaminoglycan (e.g., dextran sulfate). In some embodiments, the component of interest is a protein (e.g., a recombinantly produced protein). In some embodiments, a detection device monitors the mobile phase after it has run through the size-exclusion column.

In some embodiments, the detection device is a spectrophotometer. In some embodiments, the detection device is a UV detector, for example set to detect sample absorption at a predetermined UV wavelength or a predetermined range of UV wavelengths. It should be appreciated that UV detectors are not typically used to determine the presence or level of sample components in the context of size exclusion chromatography, because the UV absorption spectra of different components are not sufficiently distinct and the elution profiles are not sufficiently resolve or unique to be able to identify different elution peaks. However, methods described herein have an unexpected effect on glycosaminoglycan migration in size exclusion chromatography and distinguish them sufficiently from other sample components (e.g., proteins, salts, etc.) to allow a spectrophotometer, e.g., a UV detector, to be used to evaluate the presence and/or amount of glycosaminoglycan in a sample.

In some embodiments, methods disclosed herein allow for sufficient separation between protein and glycosaminoglycan fractions, for a detector that detects both protein and glycosaminoglycan absorbance wavelengths (such as a UV detector set at a single wavelength) can be used. In some embodiments, methods disclosed herein allow for sufficient focusing of the glycosaminoglycan fraction for low levels of glycosaminoglycan to be detected using a non-specific detection technique such as a UV detector. However, it should be appreciated that any detector that can detect a glycosaminoglycan can be used. Detectors that can be used according to the methods described herein include a Corona charged Aerosol Detector (CAD), an Evaporative Light Scattering Detector (ELSD), a Refractive Index (RI) detector, a Condensation Nucleation Light Scattering Detector (CNLSD), and a Nano Quantity Analyte Detector (NQAD).

In some embodiments, a sample for analysis is removed from a larger preparation (e.g., a manufacturing preparation). The analysis can be performed using separate chromatography and/or detector instruments. However, in some embodiments, a manufacturing device may be adapted to include a chromatography component having an appropriate detector configured for continuous or intermittent sample analysis.

Mobile Phase

In some embodiments, methods disclosed herein include the act of applying a mobile phase to a size-exclusion chromatography column. Generally, a sample that has been applied onto a size-exclusion chromatography column will be run through the column by applying a mobile phase to the column. The mobile phase applied to the column will have specific characteristics, e.g., salts, buffer concentration, pH that allow for a sample to run through a column.

In some embodiments, a sample is subjected to size exclusion chromatography at a pH of 6.8 or less. In some embodiments, the pH is about 6.0 or less, about 5.0 or less, about 4.0 or less, about 3.0 or less, or about 2.5 or less. In some embodiments, a sample is applied to a size-exclusion column and a mobile phase is applied to the column, wherein the mobile phase has a pH of 6.8 or less. In some embodiments, the pH of the mobile phase is about 6.0 or less, about 5.0 or less, about 4.0 or less, about 3.0 or less, or about 2.5 or less. In some embodiments, the mobile phase has a pH range of 2 to 6.8, 3 to 6.8, 4 to 6.8, 5 to 6.8, 6 to 6.8, 2 to 6, 3 to 6, 4 to 6, 5 to 6, 2 to 5, 3 to 5, 4 to 5, or 3 to 4.

In some embodiments, the chromatography material (e.g., column or other format) is prepared with a mobile phase that has a pH of 6.8 or less. In some embodiments, the sample is loaded/and or eluted using a mobile phase that has a pH of 6.8 or less. In some embodiments, the pH of the mobile phase is lower than 6.8. In some embodiments, the pH of the mobile phase is 6.0 or lower. In some embodiments, the pH of the mobile phase is 5.0 or lower. In some embodiments, the pH of the mobile phase is 4.0 or lower. In some embodiments, the pH of the mobile phase is 3.0 or lower. In some embodiments, the pH of the mobile phase is 2.5 or lower. In some embodiments, the mobile phase comprises a buffer which stabilizes the desired pH of the sample. Different pH buffers are known in the art and include, but are not limited to, citrate buffers, acetate buffers and phosphate buffers. In some embodiments, the buffer is a potassium mono-hydrogen-phosphate and potassium di-hydrogen-phosphate buffer. In some embodiments, the buffer is a sodium mono-hydrogen-phosphate and sodium di-hydrogen-phosphate buffer. In some embodiments, the concentration of the buffer is between 1 mM and 500 mM, between 2 mM and 400 mM, or between 10 and 300 mM. In some embodiments, the buffer is a 100 mM sodium phosphate buffer.

In some embodiments, the mobile phase further includes one or more salts. While not being limited to a specific mechanism, it is thought that the salt helps solubilize one or more components of a sample, and provides for a homogeneous flow of the sample through the column. In some embodiments, the salt is sodium chloride. In some embodiments, the salt is potassium chloride. In some embodiments, the salt concentration is between 1 mM and 500 mM, between 2 mM and 400 mM, or between 10 and 300 mM. In some embodiments, the salt is sodium chloride at a concentration of 200 mM.

In some embodiments, the mobile phase further includes one or more salts in addition to sodium chloride or potassium chloride. Non-limiting examples of other salts that can be used in the mobile phase (in addition to, or, instead of, sodium and/or potassium salts) include ammonium salts and calcium salts. In some embodiments, the concentration of these one or more other salts is between 10 mM and 250 mM, such as between 25 mM and 100 mM. In some embodiments, the salt concentration is 50 mM. In some embodiments, the salt concentration is less than 10 mM. In some embodiments, the salt concentration is more than 250 mM. In some embodiments, the salt concentration is 50 mM.

In some embodiments, a sample is equilibrated with the mobile phase (e.g., by dialysis or other suitable technique) prior to being subjected to chromatography (e.g., prior to being loaded on a size-exclusion column). However, a sample may be processed directly without being equilibrated with the mobile phase prior to chromatography.

In some embodiments, a column is conditioned prior to applying the sample. In some embodiments, the column is conditioned with a protein solution prior to application of the sample.

In some embodiments, the mobile phase that has run through the column (e.g., that has been eluted) comprises components of the sample. In some embodiments, the mobile phase that has run through the column is collected. In some embodiments, the mobile phase that has run through the column and that comprises sample components is collected. In some embodiments, a subset of the mobile phase that has run through the column is collected (e.g., as a fraction of the eluate). For instance, a detector at the end of the column may indicate when a component of interest (e.g., a protein such as Factor IX) is present in the mobile phase. In some embodiments, the mobile phase comprising the component of interest is collected. In some embodiments, the component of interest that has been collected is analyzed further to determine the nature of the component of interest (e.g., protein of interest or glycosaminoglycan).

In one aspect, the disclosure provides methods for separating (one or more) protein(s) from one or more glycosaminoglycans in a sample. In some embodiments, the protein is separated by collecting a subset of the mobile phase that has run through the column that comprises the protein (and that does not include the glycosoaminoglycan(s) or includes only small amounts of glycosoaminoglycan(s)). In some embodiments, the protein separated from the glycosaminoglycan includes less than 10% of the level of glycosaminoglycan present in the protein sample prior to size-exclusion column chromatography (e.g., a sample with 1 mg of protein after chromatography includes 0.01 mg of glycosaminoglycan, while prior to chromatography a sample with 1 mg of protein included 0.1 mg of glycosaminoglycan). In some embodiments, the protein separated from the glycosaminoglycan includes less than 10%, less than 5%, less than 2%, less than 1%, less than 0.5%, less than 0.1%, less than 0.05%, less than 0.001%, less than 0.0001% or less of the level of glycosaminoglycan present in the protein sample prior to size-exclusion column chromatography. In some embodiments, the protein separated from the glycosaminoglycan includes less than 20%, less than 30%, less than 40%, less than 50%, less than 60%, less than 70%, less than 80%, less than 90%, or less than 100% of the level of glycosaminoglycan present in the protein sample prior to size-exclusion column chromatography.

Applications

It should be appreciated that methods and composition described herein may be used analytically to evaluate samples and determine the presence and/or amount of one or more glycosaminoglycans in a sample. In some embodiments, an assay may be calibrated to determine whether an amount of glycosaminoglycan (e.g., dextran sulfate) in a sample is above or below a certain threshold. For example, a threshold may be set using a reference amount of glycosaminoglycan (e.g., 10 microg/ml, 5 microg/ml, 2 microg/ml, 1 microg/ml, or lower). The threshold may represent an amount above which a protein preparation should be rejected and/or further processed.

Analytical techniques described herein may be used to evaluate commercial protein preparations, for example as a quality control step, to determine whether they meet acceptable levels of purity (e.g., levels of glycosaminoglycan below a predetermined level). However, analytical techniques described herein also may be used to evaluate one or more manufacturing and/or purification processes to determine whether appropriate levels of glycosaminoglycans are present. In some embodiments, production processes may be continuously monitored using methods described herein.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: Separating Dextran from a Protein Sample

A partially purified protein manufacturing sample for the manufacturing of Factor IX-Fc is spiked with dextran sulfate (6-8 kDa) resulting in samples ranging from 1 microgram/ml to 50 microgram/ml dextran sulfate.

An aliquot of the sample is applied to a TSKgel G2000SWx1 column (Tosoh) and eluted with a mobile phase containing 100 mM sodium phosphate, 200 mM sodium chloride at pH 2.5. The eluent is monitored with UV detector (214 nm). The dextran sulfate sample is separated from the protein and elutes later than the proteins.

The quantitation of dextran sulfate in the test samples is performed using an external standard calibration curve made of dextran sulfate standards. FIG. 1 shows the linearity plot for a Factor IX-Fc sample (LP5-10-FIX-001) spiked with dextran sulfate standards.

Concentrations of dextran sulfate in a partially purified protein manufacturing sample (Factor IX-Fc) down to 2 microgram/mL can be determined. FIG. 2 shows a calibration curve for dextran sulfate standards, and several zoomed-in chromatograms including Factor IX-Fc sample alone, Factor IX-Fc formulation buffer alone, and Factor IX-Fc sample spiked with 2 microgram/mL of dextran sulfate (6-8 kDa), respectively.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method of separating a factor VIII (FVIII) protein or a factor IX (FIX) protein from glycosaminoglycan during chromatography, the method comprising:
    (i) subjecting a sample comprising one or more the FVIII or FIX proteins and glycosaminoglycan to a size-exclusion chromatography using a mobile phase having a pH of less than 3.0, and
    (ii) collecting a mobile phase fraction comprising the FVIII or FIX proteins;
    wherein the mobile phase comprises a salt;
    wherein the mobile phase fraction does not include the glycosaminoglycan or includes only small amounts of the glycosaminoglycan, and
    wherein the method does not include a use of fluorescent labeling.

2. The method of claim 1, further comprising using a detection device to determine the amount of glycosaminoglycan in the mobile phase fraction.

3. The method of claim 2, further comprising determining if the amount of glycosaminoglycan in the sample is above a threshold level.

4. The method of claim 3, wherein the threshold level is 2 microgram/ml.

5. The method of claim 2, wherein the detection device is a UV detector.

6. The method of claim 1, wherein the sample is unpurified or partially purified.

7. The method of claim 1, wherein the sample comprises a FVIII protein.

8. The method of claim 1, wherein the sample comprises a FIX protein.

9. The method of claim 1, wherein the glycosaminoglycan is negatively charged.

10. The method of claim 1, wherein the glycosaminoglycan is dextran sulfate or heparin sulfate.

11. The method of claim 10, wherein the glycosaminoglycan is dextran sulfate having a size of 6-8 kDa.

12. The method of claim 1, wherein the size-exclusion chromatography packing material and mobile phase allow for secondary interactions.

13. The method of claim 12, wherein the size-exclusion chromatography packing material is silica-based, has a pore size of between 100-200 Angstrom, and a particle size of 5 microns or less.

14. The method of claim 1, wherein the size-exclusion chromatography is performed on a silica-based size-exclusion column.

15. The method of claim 1, wherein the pH of the mobile phase is about 2.5.

16. The method of claim 15, wherein the pH of the mobile phase is 2.5.

17. The method of claim 1, wherein the salt is 200 mM NaCl.

18. The method of claim 1, wherein the FVIII protein is Factor VIIIFc.

19. The method of claim 1, wherein the FIX protein is Factor IXFc.

* * * * *